United States Patent
Wunderlich et al.

(10) Patent No.: US 10,598,626 B2
(45) Date of Patent: Mar. 24, 2020

(54) SENSOR ARRANGEMENT

(71) Applicant: Endress+Hauser Conducta GmbH+Co. KG, Gerlingen (DE)

(72) Inventors: Ingrid Wunderlich, Radebeul (DE); Michael Hanko, Dresden (DE); Christian Fanselow, Geringswalde (DE)

(73) Assignee: Endress + Conducta GmbH+Co. KG, Gerlingen (DE)

( * ) Notice: Subject to any disclaimer, the term of this patent is extended or adjusted under 35 U.S.C. 154(b) by 463 days.

(21) Appl. No.: 15/420,120

(22) Filed: Jan. 31, 2017

(65) Prior Publication Data

US 2017/0219512 A1 Aug. 3, 2017

(30) Foreign Application Priority Data

Feb. 1, 2016 (DE) .......................... 10 2016 101 715

(51) Int. Cl.
*G01N 27/333* (2006.01)
*G01N 27/416* (2006.01)
*G01N 27/403* (2006.01)

(52) U.S. Cl.
CPC ....... *G01N 27/333* (2013.01); *G01N 27/4035* (2013.01); *G01N 27/4161* (2013.01)

(58) Field of Classification Search
CPC ........... G01N 27/4166; G01N 27/4167; G01N 27/301; G01N 27/302; G01N 27/333;
(Continued)

(56) References Cited

U.S. PATENT DOCUMENTS 5,939,160 A 8/1999 Kline et al.
6,773,678 B2 * 8/2004 Cummings .......... G01N 27/283
422/560
(Continued)

FOREIGN PATENT DOCUMENTS

DE 102011080956 A1 1/2013
DE 102013101735 A1 10/2013
(Continued)

OTHER PUBLICATIONS

Search Report for German Patent Application No. 10 2016 101 715.9, German Patent Office, dated Mar. 15, 2017, 9 pp.

*Primary Examiner* — Gurpreet Kaur
(74) *Attorney, Agent, or Firm* — Kelly J. Smith; PatServe

(57) ABSTRACT

The present disclosure relates to a sensor arrangement including a housing, connectable to a process container and including a guiding passageway formed therein, and a sensor body displaceable in the guiding passageway between a first position and a second position, wherein the sensor body has at least one end section, which can be moved out of the housing and which includes at least one sensor element serving for registering a measured variable of a measured medium, wherein the at least one sensor element is arranged in the first position of the sensor body within a chamber formed in the housing and, in the second position of the sensor body, outside of the housing, and wherein the at least one end section of the sensor body has a base and a peripheral surface, wherein the at least one sensor element forms a part of the peripheral surface.

19 Claims, 6 Drawing Sheets

(58) Field of Classification Search
CPC ............. G01N 27/3335; G01N 27/416; G01N 27/4117; G01N 27/4035
See application file for complete search history.

(56) References Cited

U.S. PATENT DOCUMENTS

| | | |
|---|---|---|
| 2001/0028865 A1 | 10/2001 | Cummings et al. |
| 2011/0303006 A1* | 12/2011 | Wunderlich ......... G01N 27/283 73/431 |
| 2013/0270125 A1* | 10/2013 | Lobbert ............. G01N 27/4163 205/793 |

FOREIGN PATENT DOCUMENTS

| | | |
|---|---|---|
| EP | 2363704 B1 | 4/2015 |
| EP | 2734611 B1 | 4/2015 |

\* cited by examiner

SENSOR ARRANGEMENT

CROSS-REFERENCE TO RELATED APPLICATIONS

The present application is related to and claims the priority benefit of German Patent Application No. 10 2016 101 715.9, filed on Feb. 1, 2016, the entire contents of which are incorporated herein by reference.

TECHNICAL FIELD

The present disclosure relates to a sensor arrangement, in particular sensor arrangements for single-use containers.

BACKGROUND

Pharmaceutical, biological, biochemical and biotech processes are performed in increasing measure by means of so called single-use, process solutions, e.g. process plants applying single-use technology. Such process plants comprise pipelines or reactors, which are embodied as single-use containers. These are also referred to as disposables, respectively disposable bioreactors or single-use bioreactors, respectively single-use components. These single-use containers can be flexible containers, for example, bags, hoses or fermenters. Bioreactors or fermenters frequently have supply and drain lines, which can be embodied, for example, as hoses. There can be rigid tubular pieces inserted in the supply and drain lines. After termination of a process, the single-use container can be disposed of. In this way, complex cleaning and sterilization methods are avoided. Generally, the use of single-use containers avoids the risk of cross contamination and therewith increases process safety.

In order to monitor or control the processes, it can be necessary to measure physical or chemical, measured variables of the media contained in the single use, process containers. Examples of sensors used in such cases include optical, however, also electrochemical, potentiometric or amperometric sensors or conductivity sensors. Proved advantageous are so-called multi-sensors, which are embodied to measure a plurality of mutually differing, measured variables. Such multi-sensors have, frequently, a number of measuring transducers, wherein each measuring transducer is embodied for registering measured values of one of the measured variables to be monitored.

The processes performed in single-use containers run in a closed system, i.e., without connection to the environment outside of the single-use container. Since sterile conditions are frequently required, the single-use container must be sterilized before introduction of the process media. Gamma radiation is frequently used for this purpose in biochemical, biological, biotechnological and pharmaceutical applications. Also, while the processes are running in a single-use fermenter or single-use reactor, the penetration of impurities, such as germs, from the environment into the interior of the single-use container must be prevented, in order not to degrade or corrupt the process. The same holds also for supply and drain lines communicating with the single-use fermenter or single-use reactor.

One or a number of sensors integrated in the single-use container can be sterilized together with the single-use container. As a result of the sterilizing and/or for the case in which a longer time span lies between the sterilizing and the start-up of the single-use container and the integrated sensors, properties of the integrated sensors can change, which can lead to a change of the respective sensor characteristic lines, e.g., to a zero point drift. Potentiometric and amperometric sensors frequently include membranes, which ideally should be stored moist. Moist storage assures that the sensors output reliable measured values immediately from start-up.

Another complication is the fact that sterilizing by means of gamma radiation required for many biochemical and biotech processes can lead to the destruction of electronic components of the sensors. It has therefore been provided, for example, in DE 10 2011 080 956 A1, to embody sensors, which are integrated into the wall of single-use containers to be sterilized, as analog, single use sensors and to connect them, only after sterilizing, releasably with an electronics unit arranged outside of the single-use container and comprising sterilizable components. The electronics unit is embodied to process the analog measured values provided by the sensor further. The electronics unit can, after terminating the process, be used again and be connected with a new, sterilized, single use sensor in another process installation. Since the complete measuring path, which includes the analog sensor and the electronics unit, is present only upon start-up, it would likewise be desirable in such cases to provide, directly before start-up, an efficient calibration, verification or even adjusting of the sensors integrated in the single-use container.

Known from EP 2734611 B1 is a sensor arrangement, which is securable on a process container, and which includes a housing, in which a probe tube can be moved axially into and out of the process container. Accommodated in the probe tube is a sensor, e.g., a pH sensor, whose end section, which must be brought in contact with a measured medium for registering measured values of a measured variable, can protrude out of the probe tube. Connected with the probe tube via an axially extending strut is a disc shaped closure element. In a first position of the probe tub moved into the housing, the closure element closes the housing at the process container end and the sensor element of the sensor is arranged in a chamber formed within the housing. Contained in this chamber can be a liquid, for example, a calibration liquid. In a second position of the probe tube moved out of the housing, the closure element is arranged spaced out of the housing, so that the chamber formed within the housing is open to the process container, and the sensor can contact a medium contained in the process container for performing measurements. Since the closure element is arranged spaced from the sensor element in the axial direction toward the process container, the probe tube must be moved a relatively great distance into the process container, in order to bring the sensor into contact with a measured medium contained in the process container. Additionally, in the case of this known sensor arrangement, a movement of liquid from the chamber formed within the housing into the process container, respectively a movement of a medium from the process container into the chamber, cannot be excluded.

Described in EP 2363704 B1 is a sensor arrangement with a sensor system to be calibrated and a compartment containing a calibration means, wherein the sensor system and the compartment are accommodated in a housing movably relative to one another. The housing is connectable with a process container. The sensor system can be calibrated in the compartment and then by an irreversibly executable, relative movement between the sensor system and the compartment be brought into a measurement ready position. The apparatus is relatively complicated in construction. For preventing movement of liquid from the chamber formed within the housing into the process container, a septum is provided, through which a sensitive element of the sensor can be moved. Since the movement of the sensor is irreversible, the sensor can no longer be moved back. Therewith, indeed, a movement of process media from the process container into the compartment is suppressed. On the other hand, therewith, a renewed calibration or regeneration of the sensor system in the compartment after a certain period of use is excluded.

BRIEF SUMMARY

It is therefore an object of the present disclosure to provide an improved sensor arrangement having at least one sensor element for registering a measured variable of a measured medium in a process container, for example, a single use-process container, enabling a fast start-up and a sufficient accuracy of measurement and quality of the registered measured values. Advantageously, the sensor arrangement should have a construction which is simpler than that of the sensor arrangements known from the state of the art.

This object is achieved by the sensor arrangement defined in independent claim 1. Further embodiments are set forth in the dependent claims.

The sensor arrangement of the present disclosure includes a housing, which is connectable with a process container and in which a guiding passageway is formed, and a sensor body displaceable in the guiding passageway in the axial direction between a first position and a second position, wherein the sensor body has at least one end section, which can be moved out of the housing and includes at least one sensor element serving for registering a measured variable of a measured medium, wherein the at least one sensor element is arranged in the first position of the sensor body within a chamber formed in the housing and, in the second position of the sensor body, outside of the housing, wherein the at least one end section of the sensor body has a base and a peripheral surface, and wherein the at least one sensor element forms a part of the peripheral surface.

Since the at least one sensor element forms a part of the peripheral surface, other components for accommodating the sensor, e.g., a probe tube, can be omitted. While the sensor arrangement known from EP 2734611 B1 requires a closure element spaced axially toward the process container from the sensor element, in order to seal the housing interior from the process container when the probe tube is pulled back into the housing of the sensor arrangement, in the sensor arrangement of the present disclosure, the housing can be sealed liquid-tight by the process end of the sensor body in the first position of the sensor body, in which the sensor element is arranged within the chamber formed in the housing. A septum for separating the housing of the sensor arrangement from the process container is likewise not required. Thus, the sensor arrangement of the present disclosure can be embodied very simply of few components. The positioning of the sensor element on the peripheral surface makes it possible, moreover, to wipe off substances clinging to the peripheral surface surrounding the sensor element in the case of movement into the process container, respectively in the case of the movement out of the process container, so that carryovers of substances between the chamber and the process container can be prevented, even when the sensor element is moved multiple times out of the housing and back into the housing.

The process container can be, for example, a process container of single-use, disposable, technology, such as already described above. It may be formed of a plastic with hygienic certification and have a flexible or fixed wall. The container with the integrated sensor arrangement can be sterilized by means of gamma radiation up to 50 kGy and then be immediately placed in operation or stored for a longer period of time. The sensor arrangement can, in this case, likewise be formed at least partially of a plastic, such as a plastic with hygienic certification.

In an embodiment, at least one part of the peripheral surface is formed by a housing wall of a housing part of the sensor body, wherein the at least one sensor element is integrated into the housing wall in such a manner that the sensor element is one-piece with the housing wall or that the at least one sensor element is connected by material bonding with an opening of the housing wall in such a manner that the at least one sensor element closes the opening of the housing wall. The sensor body can be formed of a single housing part or a number of housing parts connected with one another. The peripheral surface can be an external surface or a surface region of the wall forming the peripheral surface.

The at least one sensor element can, for example, include a membrane, which closes a chamber surrounded by the housing wall.

In an embodiment, the at least one sensor element can be embodied as an insert in the housing wall, for example, an annular insert, extending around a rotational symmetry axis, such as a cylindrical axis, of the housing wall. If the sensor element comprises a membrane or is embodied as a membrane, it can be embodied as an insert in the housing wall, for example, an annular insert, extending around a rotational symmetry axis, such as a cylindrical axis, of the housing wall.

The housing part, whose housing wall forms at least one part of the peripheral surface, can be embodied, for example, with cylindrical or annular shape and the at least one sensor element, that is, the membrane (for the case, in which the sensor element comprises a membrane), can close the housing part on an end as an appendage of the housing, such as a capsule shaped appendage or an appendage embodied as an annular cup. The appendage in capsule or annular cup shape can be embodied, for example, as one-piece with the housing part or be connected with an end of the housing part by material bonding. Fusion bonding or adhesion can be used for connection of the housing part with the appendage.

The sensor arrangement can be embodied as a potentiometric sensor arrangement having a measuring half cell and a reference half cell. The potentiometric sensor arrangement can be embodied, for example, as a potentiometric pH sensor or as an ion-selective electrode for determining the concentration, respectively activity, of a certain kind of ion.

In this embodiment, a measuring half cell chamber and a reference half cell chamber can be formed in the sensor body. Accommodated in the measuring half cell chamber can be an inner electrolyte. In an embodiment where the potentiometric sensor arrangement serves for determining pH-value, the inner electrolyte can be a buffer solution with a predetermined concentration of chloride ions. Correspondingly contained in the reference half cell chamber can be a reference electrolyte, e.g., a KCl solution of predetermined concentration. Arranged in the measuring half cell chamber can be a potential sensing element, which contacts the inner electrolyte and which is electrically conductively connected with a contact location outside of the measuring half cell chamber. The potential sensing element can be a metal wire, e.g., a chloridized silver wire. Arranged in the reference half cell chamber can be a reference element, for example, a chloridized silver wire contacting the reference electrolyte and electrically conductively connected with an additional contact location outside of the reference half cell chamber. Arranged in the sensor body, outside of the reference half cell chamber and the measuring half cell chamber, can be a measurement circuit, which is connected with the two contact locations and is embodied to register a potential difference between the potential sensing element and the reference element. The measurement circuit can be embodied to be connectable with a superordinated electronic data processing system by means of a plugged connection.

At least a part of the wall of the measuring half cell chamber can form at least one part of the peripheral surface of the end section of the sensor body, wherein the at least one sensor element comprises an ion-selective membrane, such as a pH glass membrane, which is integrated into the part of the wall of the measuring half cell chamber forming the part of the peripheral surface of the end section. For the case, in which the sensor element is a pH glass membrane, the wall of the measuring half cell chamber can be formed of glass, wherein the glass membrane can be fusion bonded or adhered in the outer wall of the measuring half cell chamber.

The measuring half cell chamber can be formed in a housing part of the sensor body. The ion-selective membrane and the housing part can be embodied as described above.

At least a part of a wall of the reference half cell chamber can form at least one part of the peripheral surface of the end section of the sensor body, wherein in the part of the wall of the reference half cell forming the part of the peripheral surface of the end section an electrochemical liquid junction, such as a diaphragm, is arranged. In the first position of the sensor body, the liquid junction is arranged within the chamber formed in the housing and, in the second position of the sensor body, the liquid junction is arranged outside of the sensor housing. The diaphragm can be formed, for example, of a porous ceramic. The wall of the reference half cell chamber can be formed of a plastic, preferably one having hygienic certification. The liquid junction provides an electrolytic contact between the reference electrolyte contained in the reference half cell space and a medium contacting the peripheral surface.

In an embodiment, the at least one end section of the sensor body can be embodied cylindrically, wherein the measuring half cell chamber or the reference half cell chamber is formed in a first, annular housing part of the sensor body, which surrounds at least one section of a second housing part of the sensor body. The respective half cell chamber not formed in the annular housing part can be formed in the second housing part.

In all embodiments described herein, the at least one end section of the sensor body can comprise a supplemental sensor element, for example, a temperature detector.

In an additional embodiment, the sensor body can have a number of end sections, for example, cylindrically embodied, end sections, which can be moved out of the housing and which extend essentially parallel to one another, wherein each of the end sections is formed by at least one section of a housing part, such as a cylindrical, housing part, of the sensor body, and wherein the measuring half cell chamber is formed in a housing part forming a first end section, and the reference half cell chamber is formed in a housing part forming a second end section. As in the case of the above described embodiments, in the first position of the sensor body, the sensor element of the measuring half cell and the electrochemical liquid junction of the reference half cell are arranged within the chamber formed in the housing and, in the second position of the sensor body, arranged outside of the housing.

In this embodiment, a housing part of the sensor body forming a third end section can comprise a supplemental sensor element, for example, a temperature detector.

The chamber formed in the housing can be formed between the guiding passageway and the peripheral surface of the at least one end section of the sensor body, wherein the chamber is bounded by at least one sealing element extending around the end section of the sensor body. The chamber can be formed, for example, by at least two ring seals arranged axially spaced from one another and extending around the end section of the sensor body. Alternatively, the chamber can be surrounded completely by a single sealing element.

The at least one sealing element can be arranged in the housing and bear against the peripheral surface of the end section of the sensor body, wherein the at least one sensor element in the case of the moving of the sensor body from the first position into the second position travels over the sealing element. In an advantageous embodiment, the sealing element can have a wipe off element, for example, embodied as a peripheral protrusion, which serves for wiping off substances clinging to the peripheral surface, in particular the sensor element.

Communicating with the chamber can be at least one liquid inlet, such as a closable liquid inlet, and at least one liquid outlet, such as a closable liquid outlet.

In an embodiment advantageous for storing the sensor arrangement over a longer period of time, the sensor body can be located in the first position, wherein there is contained in the chamber a liquid, such as a calibration liquid and/or an electrolyte solution, which contacts the sensor element. The sensor element stored wet, in this way, is immediately ready for use in the case of placing the sensor arrangement in service.

The housing of the sensor arrangement can be connected with a process container by conventional joining technology, for example, by a mechanical, releasable connection, by adhesive, by fusion or by welding. In the state of being connected with the process container, the end face of the at least one end section of the sensor body, or the end faces of the number of end sections of the sensor body, point(s) toward the interior of the process container.

BRIEF DESCRIPTION OF THE DRAWINGS

The present disclosure will now be described in greater detail in the following based on examples of embodiments illustrated in the drawing, the figures of which show as follows.

DETAILED DESCRIPTION

Figure 1:
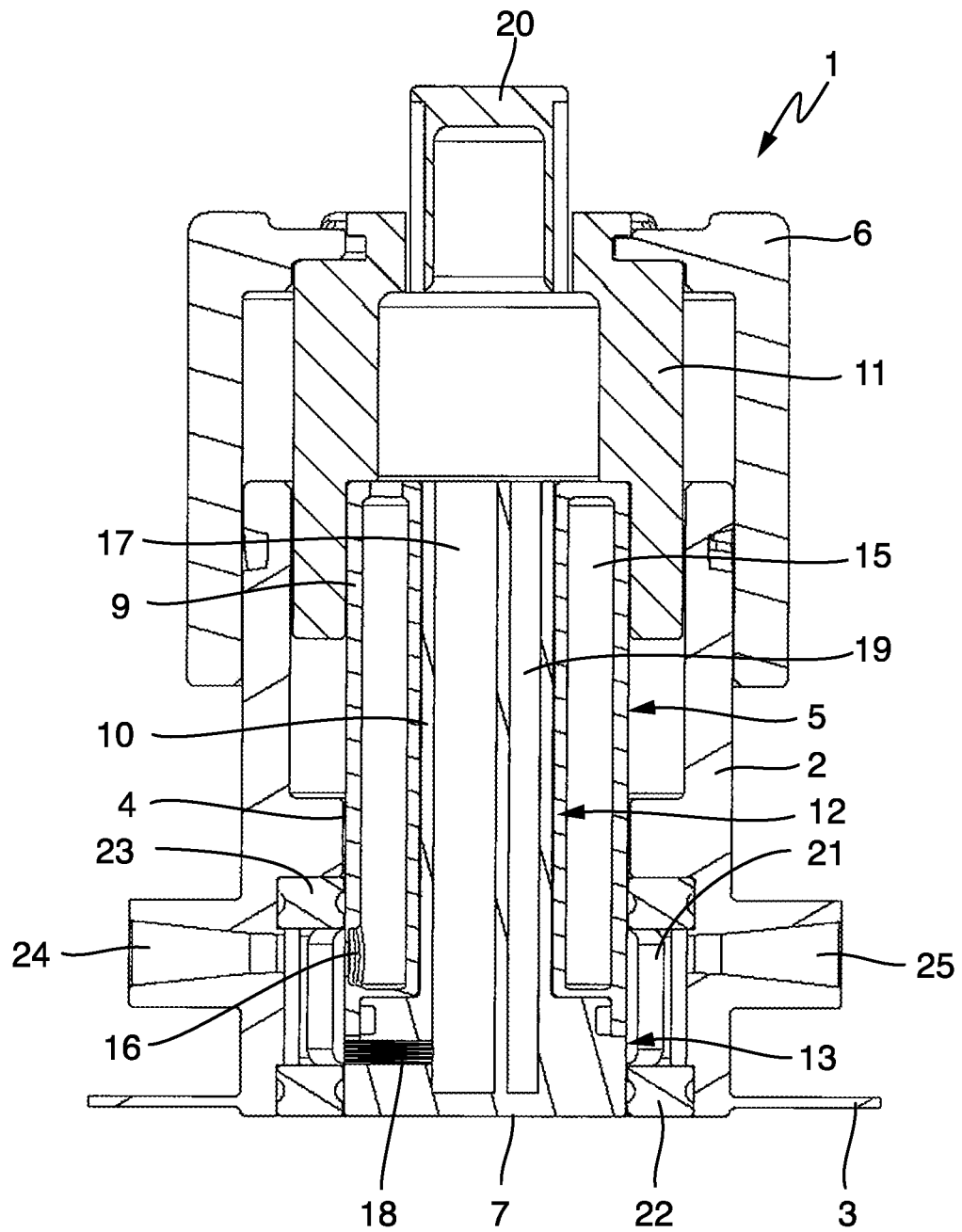
FIG. 1 shows a longitudinal section of a sensor arrangement of a first example of an embodiment with a sensor body in a first position.
Figure 2:
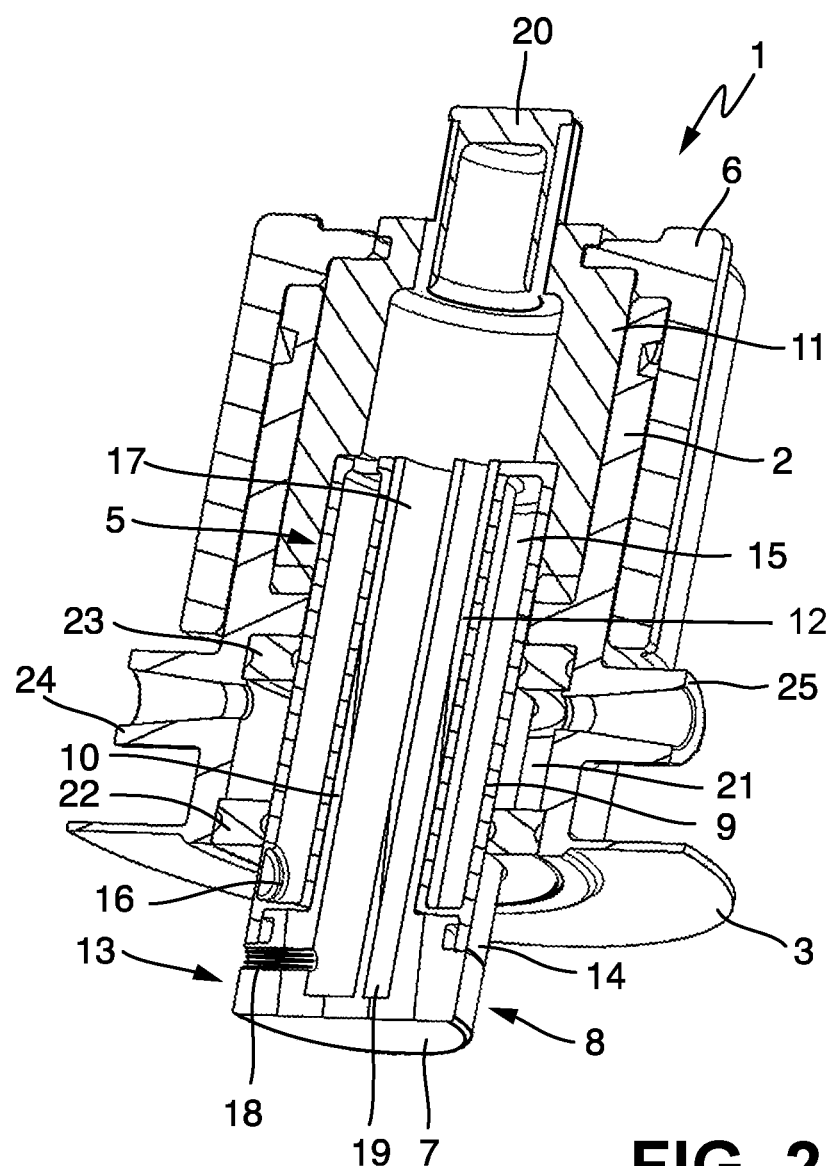
FIG. 2 shows a perspective longitudinal section of the sensor arrangement of the first example of an embodiment with the sensor body in a second position.

FIGS. 1 and 2 show a first example of a sensor arrangement 1 with a housing 2 formed of a plastic with hygienic certification. The housing is connectable with a process container, such as a process container of single use technology, e.g., a fermenter or a hose or pipeline with a rigid or flexible wall of a plastic with hygienic certification. For this, the housing 2 includes on an end a connection rail 3, which can be adhered or welded with the wall of the process container.

Formed in the housing 2 is a guiding passageway 4, in which a sensor body 5 is arranged to be axially movable. Serving for moving the sensor body 5 is a shift handle 6, which is connected with the rear end of the sensor body 5, opposite the connection rail 3. The shift handle 6 comprises a shell extending over a rear side section of the housing. The shell is rigidly connected with the sensor body 5, so that an axial movement of the shell towards the connection rail 3, or toward the process container, moves the sensor body 5 in the axial direction toward the process container. Correspondingly, an axial movement of the shell from the connection rail 3 away from the process container draws the sensor body 5 back into the housing 2. The two end positions reachable by moving the sensor body 5 are shown in FIGS. 1 and 2, respectively. FIG. 1 shows the sensor body 5 in a first position completely position within the housing 2, so that only its base 7 still contacts the environment, i.e., for the case in which the housing is connected with a wall of a process container, contacts the interior of the process container. FIG. 2 shows, in a second position, an end section 8 of the sensor body 5 moved out of the housing 2. For the case, in which the housing 2 is connected with a wall of a process container, the end section 8 in this position of the sensor body 5 protrudes into the process container. Both end positions can be predetermined by stops formed in the shift handle 6, the housing 2 and/or the sensor body 5. Also, those skilled in the art can provide means for releasably locking the end positions.

Sensor body 5 is formed of a number of housing parts, namely an annular, first housing part 9, a second housing part 10, which has a first axial section 12 surrounded by the first housing part 9, and a third housing part 11, in which the first and second housing parts 9, 10 are held and which is connected with the shift handle 6.

The outer diameter of the first axial section 12 fits the inner annular diameter of the first housing part 9, so that the inner lateral surface of the first housing part 9 lies against the outer lateral surface of the second housing part 10 in its first axial section 12. The second housing part 10 includes a second axial section 13 adjacent the first section 12. The outer diameter of the second axial section 13 is the same as the outer annular diameter of the first housing part 9. The transition between the second and first axial sections is formed by a step-shaped widening of the outer diameter of the second housing part 10, so that the first housing part 9 contacts the step-shaped widening. Since the outer diameter of the second housing part 10 is the same as the outer annular diameter of the first housing part 9, the end section 8 of the sensor body 5 has a cylindrical shape with a peripheral surface 14, which corresponds to the cylindrical lateral surface of the end section 8, as shown in FIG. 2.

In the example of an embodiment illustrated here, the sensor arrangement 1 comprises a potentiometric sensor having a pH-measuring half cell and a reference half cell. The first housing part 9 in the example of an embodiment illustrated here is formed of glass and serves as pH-measuring half cell. Formed in the housing part 9 is a measuring half cell chamber 15, in whose external wall there is arranged an opening closed by a pH glass membrane 16. The pH glass membrane 16 is arranged in the part of the wall of the housing part 9 forming the peripheral surface 14, so that in the first position of the sensor body 5 illustrated in FIG. 1 it is arranged within the housing 2 and in the second position of the sensor body 5 illustrated in FIG. 2 it is arranged outside of the housing 2.

The second housing part 10 serves, in the example of an embodiment illustrated in FIGS. 1 and 2, as reference half cell and is formed of a plastic with hygienic certification. Formed in the second housing part 10 is a reference half cell chamber 17. Arranged in the second axial section 13 of the housing part 10 for connecting the reference half cell chamber 17 with the environment of the housing part is an electrochemical liquid junction 18, which in the present example is formed by a porous ceramic diaphragm arranged in a passageway through the wall. Liquid junction 18 is arranged in a part of the wall of the housing part 10, which forms a part of the peripheral surface 14, so that the liquid junction 18 in the first position of the sensor body 5 illustrated in FIG. 1 is arranged within the housing 2 and in the second position of the sensor body 5 illustrated in FIG. 2 outside of the housing 2. Formed in the present example in the second housing part 10 is, moreover, another chamber 19, in which a temperature detector (not shown in FIGS. 1 and 2) may be accommodated.

Accommodated in the measuring half cell chamber 15 is an inner electrolyte. The inner electrolyte in the present example is a buffer solution having a predetermined chloride concentration. Contained in the reference half cell chamber 17 as reference electrolyte is a KCl solution of predetermined concentration. Arranged in the measuring half cell chamber 15 is a potential sensing element, which contacts the inner electrolyte and which is connected electrically conductively with a contact location outside of the measuring half cell chamber (not shown in the figures). The potential sensing element can be a metal wire, e.g. a chloridized silver wire. Arranged in the reference half cell chamber 17 is a reference element, for example, a chloridized silver wire, which contacts the reference electrolyte and is electrically conductively connected with an additional contact location outside of the reference half cell chamber (not shown in the figures). Both half cell chambers 15, 17 are sealed on their rear ends in conventional manner, for example, by means of a plastic potting material or by fusion or adhesion. Arranged outside of the reference half cell chamber 17 and the measuring half cell chamber 15 in the sensor body 5 or in the housing 2 can be a measurement circuit, which is electrically conductively connected with the two contact locations and which is embodied to register a potential difference between the potential sensing element and the reference element (not shown in the figures). The measurement circuit can be connected by means of a plugged connection between a plug head 20 connected with the housing 2 and a complementary counterpart (not shown) connected with a superordinated electronic data processing system for transmission of measurement signals and/or data.

Formed between the peripheral surface 14 of the sensor body 5 and the inner wall of the housing 2 is a chamber 21, which is bounded by two sealing elements 22, 23 spaced axially from one another and sealed from the process container or the environment. Communicating with the chamber 21 are a supply line 24 and a drain line 25, via which a liquid, for example, a cleaning liquid, a rinsing liquid or a calibration liquid, can be fed to and drained from the chamber 21. The supply line 24 and the drain line 25 are preferably closable by means of valves or sterile connectors (not shown in FIGS. 1 and 2). In the first position of the sensor body 5 (shown in FIG. 1) both the liquid junction 18 as well as also the pH glass membrane 15 are arranged within the chamber 21.

A moist storage of the glass membrane 15 and the liquid junction 18 can be provided by having the chamber 21 filled with liquid during storage of the sensor arrangement 1. Immediately before placement in service, a calibration can be performed in the same liquid. Alternatively, the liquid can first be removed from the chamber 21 via the drain line 25 and then a calibration liquid introduced into the chamber 21 via the supply line 24, in order to conduct a calibration of the potentiometric sensor arrangement 1 in chamber 21. Then, the chamber 21 can be emptied via the drain line 25 before the sensor body 5 is moved into the second position 2 (shown in FIG. 2) for performing measurements. In this way, a transporting of calibration liquid from the chamber 21 into the process container can be avoided.

The potentiometric sensor arrangement 1 can be calibrated during operation by moving the sensor body 5 back into the first position and introducing anew a calibration liquid into the chamber 21. During the retraction of the sensor body 5, the peripheral surface 14 of the sensor body 5 slides along the sealing element 22, so that substances clinging to the peripheral surface 14 are wiped off and do not get into the chamber 21. Advantageously, the sealing element 22 can have one or more wipe off elements, e.g., in the form of annular projections, in order to strengthen this effect further.

Figure 3:
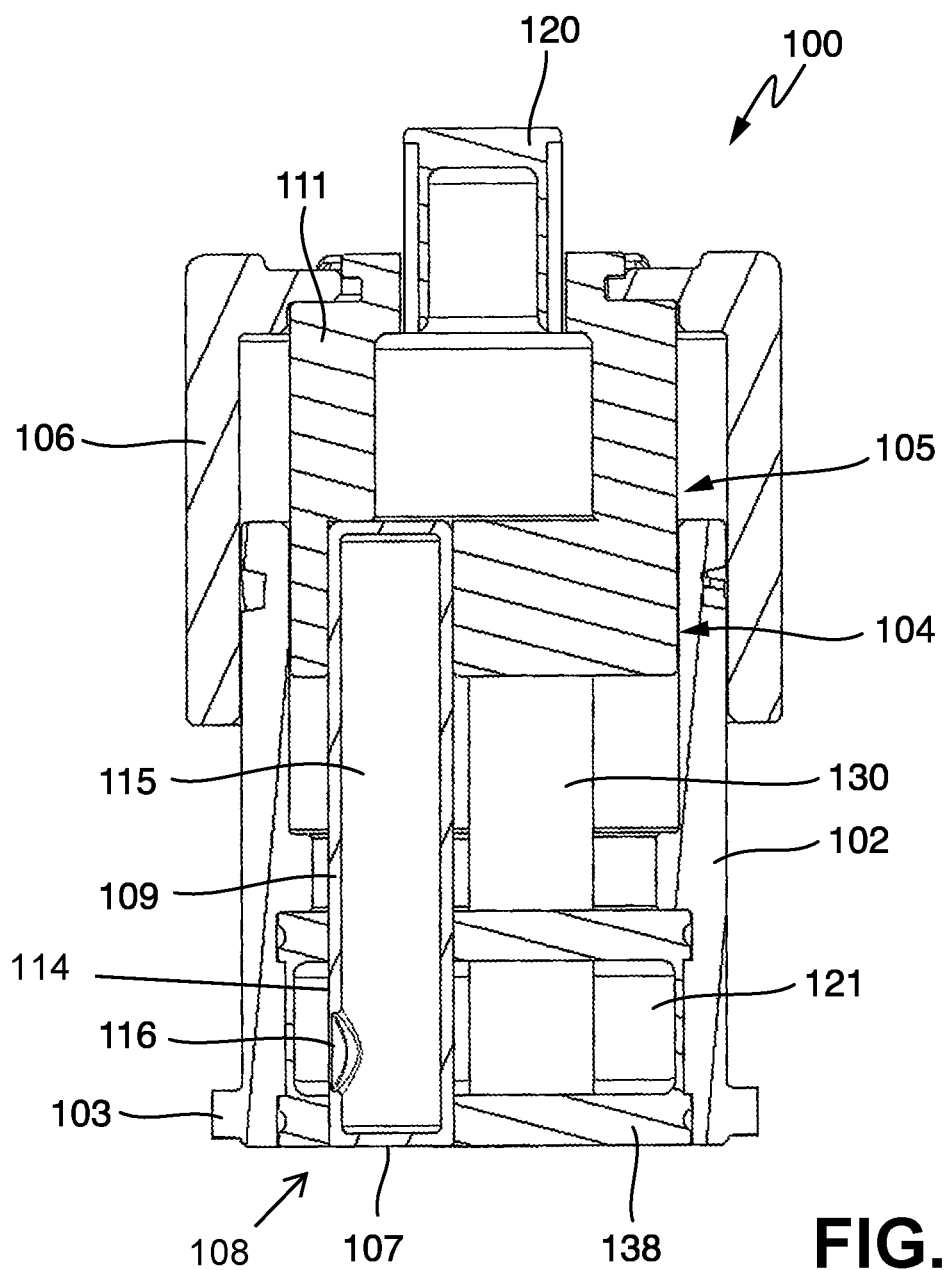
FIG. 3 shows a longitudinal section of a sensor arrangement of a second example of an embodiment with a sensor body in a first position.
Figure 4:
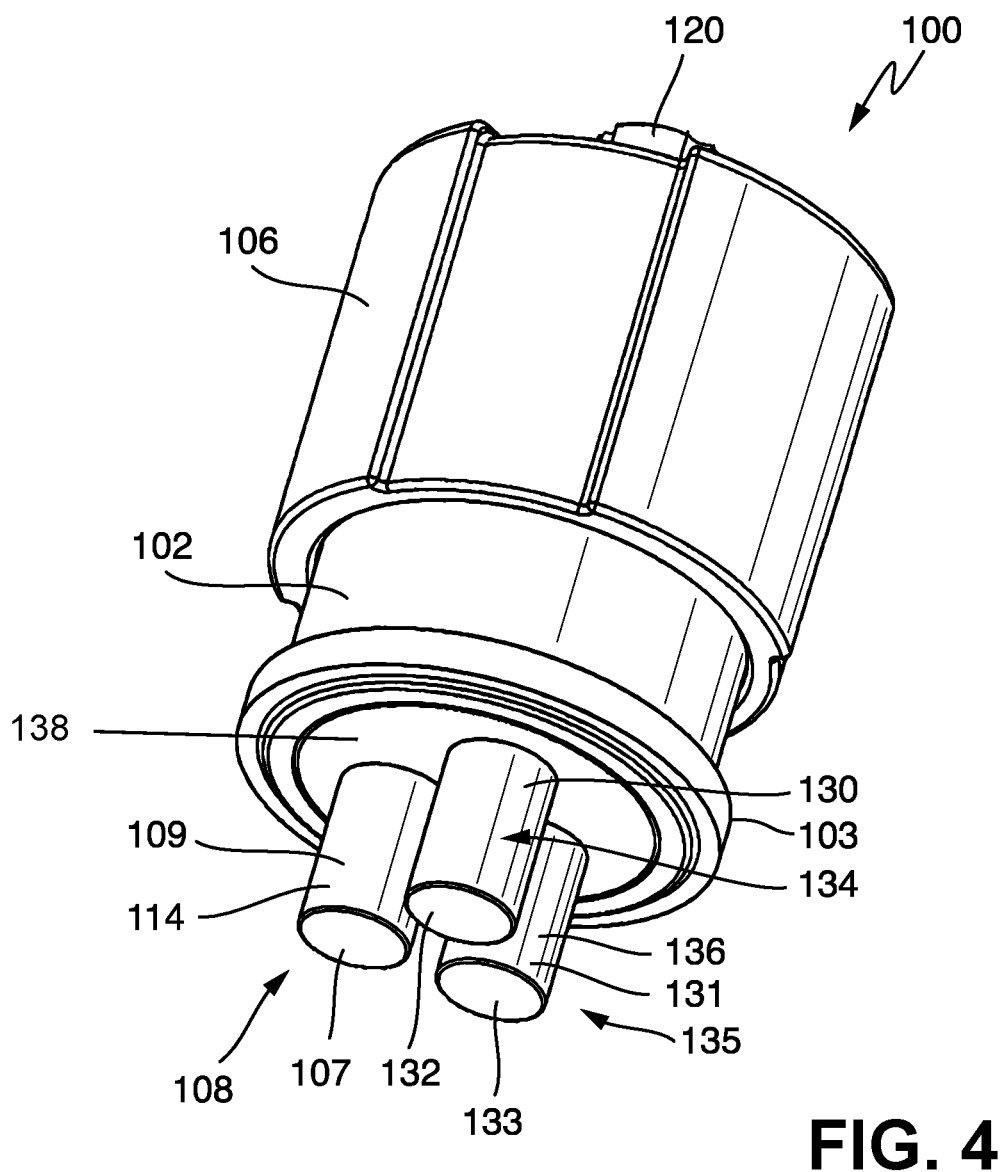
FIG. 4 shows a perspective view of the sensor arrangement of the second example of an embodiment with the sensor body in a second position.

FIGS. 3 and 4 show schematically a second example of an embodiment of a potentiometric sensor arrangement 100. Sensor arrangement 100 includes a housing 102 affixable in a wall of a process container. Housing 102 includes a connection rail 103, which can be affixed in an opening provided in the wall of the process container releasably or durably, e.g., by adhesion or welding.

Arranged in the housing 102 is a sensor body 105, which is movable in the axial direction in a guiding passageway 104, as shown in FIG. 3. Sensor body 105 includes a number of housing parts, namely a first housing part 111, which extends in the guiding passageway 104, as well as three cylindrical housing parts 109, 130 and 131, which are secured in the first housing part 111. (The cylindrical housing part 131 is not observable in the cross-sectional view of FIG. 3).

Serving for moving the sensor body is a shift handle 106 connected with the first housing part 111. Shift handle 106 can be embodied as described based on the embodiment illustrated in FIGS. 1 and 2. FIG. 3 shows the sensor body 105 in a first position, in which the sensor body 105 is located completely within the housing 102, so that only the end faces 107, 132 and 133 of its end sections 108, 134, 135 are in contact with the housing environment or, for the case in which the sensor arrangement 100 is connected with a process container, with the interior of the process container. Only the end face 107 of end section 108 is shown in the cross-sectional view of FIG. 3. FIG. 4 shows the sensor body 105 in a second position, in which its end sections 108, 134, 135 have been moved out of the housing 102, so that they can be brought in contact with a measured medium. Sensor body 105 can be moved between these two end positions illustrated in FIGS. 3 and 4, wherein the end positions can be predetermined by stops or detents.

A first housing part 109 of the three cylindrical housing parts 109, 130, 131 serves as measuring half cell of the potentiometric sensor arrangement 100 and, in the example of the embodiment shown, is formed of glass. Fused into a peripheral surface 114 of the housing wall forming end section 108 is a pH glass membrane 116. In the first position of the sensor body 105 (FIG. 3), the pH glass membrane 116 is located within the housing 102, while, in the second position of the sensor body 105 (FIG. 4), the pH glass membrane 116 is located outside of the housing 102.

A second cylindrical housing part 131 serves as reference half-cell of the potentiometric sensor arrangement and is formed of a plastic with hygienic certification in the example of an embodiment shown in FIG. 4. Arranged in the wall forming the peripheral surface 136 of the end section 135 is an electrochemical liquid junction (not shown in the figures), which can be embodied analogously to the electrochemical liquid junction of the first example of an embodiment.

A third cylindrical housing part 130 contains a temperature detector. The half cells can be embodied in detail based on the first example of an embodiment. The sensor arrangement can further utilize a measurement circuit, which is connectable via the plug head 120 with a superordinated unit, analogously as described for the first example of an embodiment.

As shown in FIG. 3, formed between the peripheral surfaces 114, 136 of the cylindrical end sections 108, 134, 135 of the sensor body 105 and the inner wall of the housing 102 is a chamber 121, which is sealed from the environment of the housing 102 and the process container by means of a sealing element 138 surrounding the chamber 121. Sealing element 138 includes openings, in which the end sections 108, 134 and 135 of the sensor body 105 are sealedly guided.

Analogously, as described in connection with the embodiment of FIGS. 1 and 2, the glass membrane 116 and the electrochemical liquid junction can in the first position of the sensor body 105 (FIG. 3) be stored moistly within the liquid in the chamber 121. In corresponding manner, a calibration of the sensor arrangement 100 can be performed with the liquid contained in the chamber. A transporting of liquid from the chamber 121 into the process container is prevented by wiping substances clinging on the peripheral surfaces 114, 136 of the end sections 108, 134, 135 of the sensor body 105 and the sensor elements, e.g., the glass membrane 116 and a electrochemical liquid junction, against the sealing element 138. Equally, a transporting of substances from the process container into the chamber 121 is excluded.

Figure 5:
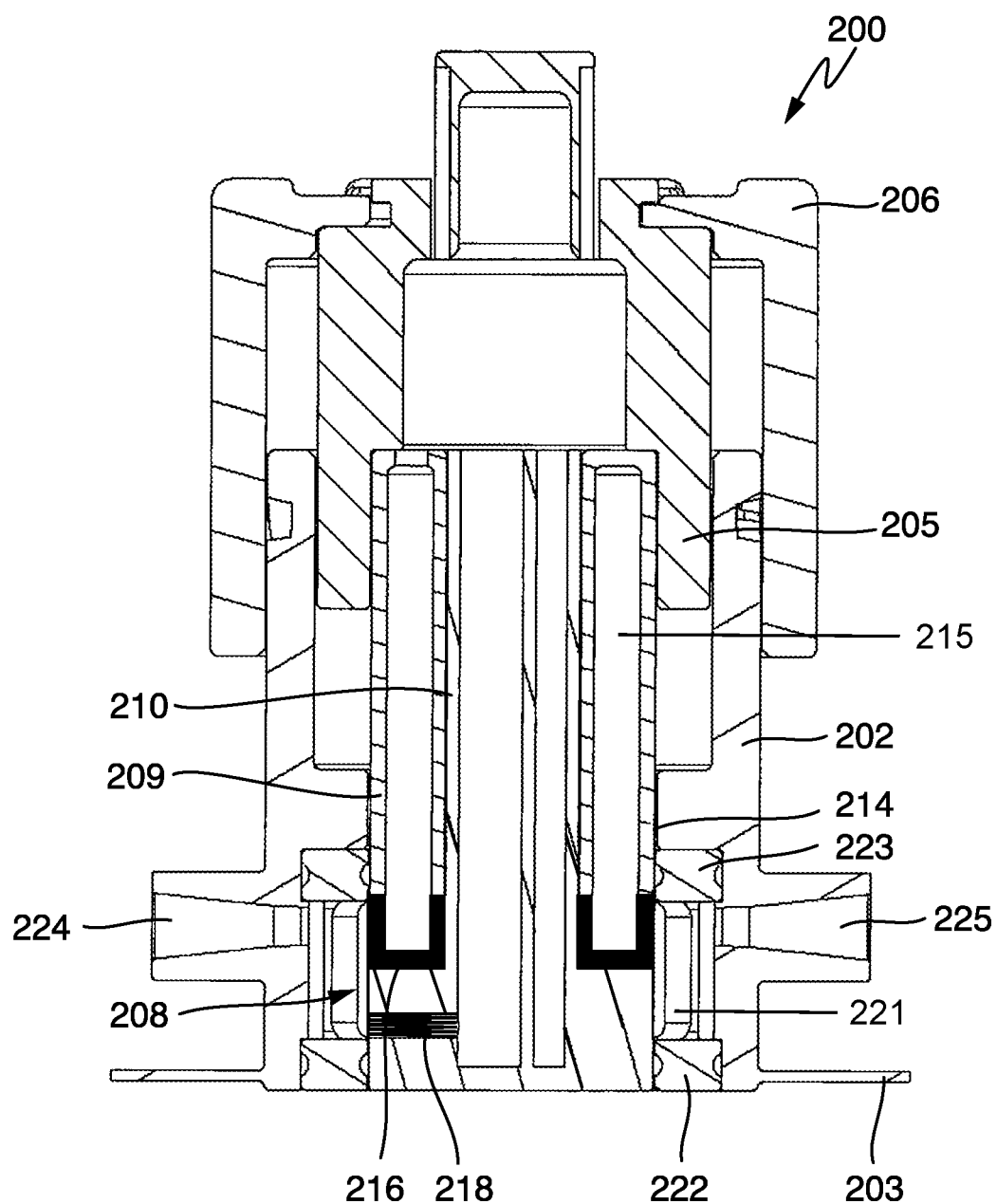
FIG. 5 shows a longitudinal section of a sensor arrangement of a third example of an embodiment.

FIG. 5 shows a further example of an embodiment of a potentiometric sensor arrangement 200. Sensor arrangement 200 is essentially embodied similarly to the sensor arrangement 1 shown in FIGS. 1 and 2 and can be affixed in a wall of a process container by means of a connection rail 203. Like the sensor arrangement 1 shown in FIGS. 1 and 2, sensor arrangement 200 includes a housing 202 and a sensor body 205, which is movable in the housing 202 axially guided between a first position (shown in FIG. 5) and a second position corresponding to the position of the sensor body 105 illustrated in FIG. 2. Enabling this movement is a shift handle 206 connected with the sensor body 205. The shift handle 206 is embodied analogously to the shift handle of the sensor arrangement 1 of the first example of an embodiment. Formed in the housing 202 is a chamber 221, which is bounded liquid tightly from the environment by two sealing elements 222, 223 arranged in the housing wall and bearing against the sensor body 205. Communicating with the chamber 221 are a liquid supply line 224 and a liquid drain line 225. As in the first example of an embodiment (i.e., as shown in FIGS. 1 and 2), in the first position, the peripheral surface 214 of the process-side end section 208 of the sensor body 205 is arranged completely within the housing 202 and in the chamber 221, while, in the second position, the process side end section 208 is translated out of the housing 202, so that the peripheral surface 214 can be brought into contact with a measured medium.

In the third example of an embodiment illustrated in FIG. 5, as in the case of the sensor arrangement 1 of the first example of an embodiment, sensor arrangement 200 comprises a potentiometric sensor having a pH-measuring half cell and a reference half cell. The measuring half cell is formed in a first housing part 209 of glass and the reference half cell is formed in a second housing part 210 of a plastic, preferably a plastic with hygienic certification.

A pH glass membrane 216 of the measuring half cell has in the third example of an embodiment the shape of an annular cup, which closes the housing part 209 on its process-side end. The cup-shaped glass membrane 216 can be fused onto the housing part 209 as an appendage. The measuring half cell chamber 215 comprising the housing part 209 and the glass membrane 216 can, such as described based on the first example of an embodiment, contain an inner electrolyte and a potential sensing element, which is contacted by a measurement circuit.

The second housing part 210 serves in the example of an embodiment illustrated here as a reference half cell and is embodied in similar manner to that of the housing part 10 of the sensor arrangement illustrated in FIGS. 1 and 2. For example, it includes an electrochemical liquid junction 218 arranged in its peripheral wall and embodied as a diaphragm. The annular housing part 209 surrounds an axial section of the second housing part 210. In such case, the outer diameter of the first housing part and a section of the second housing part 210 extending on the process-side farther than the first housing part 209 are so matched to one another that the end section 208 of the sensor body 205, which can be moved out of the housing 202, has a unified cylindrical shape with a peripheral surface 214.

As in the case of the sensor arrangement 1 of the first example of an embodiment, formed in the second housing part 210 is a reference half cell chamber, in which are arranged a reference electrolyte and a reference element, which is connected with the measurement circuit, so that the measurement circuit can register a potential difference between the measuring half cell and the reference half cell.

In the position of the sensor body 205 moved out of the housing 202, both the liquid junction 218 and the outer, surrounding area of the membrane 216 arranged in the peripheral surface 214, come in contact with a measured medium. In the first position of the sensor body 205 illustrated in FIG. 5, both are arranged in the chamber 221 and can be calibrated or cleaned there.

Otherwise, the sensor arrangement 200 is embodied substantially equally to that of the sensor arrangement 1 of the first example of an embodiment shown in FIGS. 1 and 2.

Figure 6:
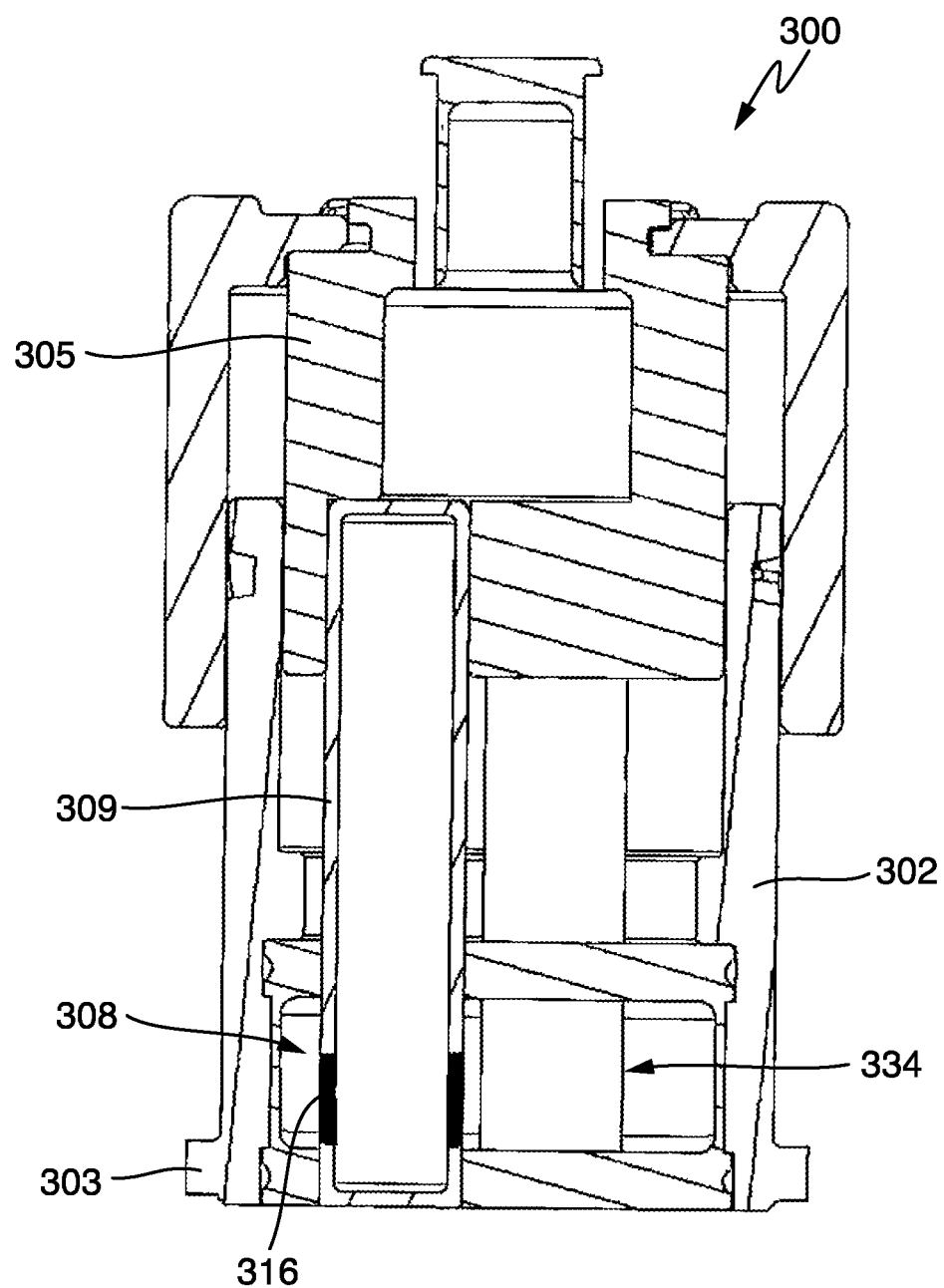
FIG. 6 shows a longitudinal section of a sensor arrangement of a fourth example of an embodiment.

FIG. 6 shows a potentiometric sensor arrangement 300 for measuring the pH-value of a measured medium according to a fourth example of an embodiment. The sensor arrangement 300 is essentially embodied identically to the sensor arrangement 100 shown in FIGS. 3 and 4 and can, such as in the case of the sensor arrangement 100, be affixed in a wall of a process container by means of a connection rail 303.

As in the case of the sensor arrangement 100 shown in FIGS. 3 and 4, sensor arrangement 300 includes in a fourth example of an embodiment a housing 302 and, held movably therein, a sensor body 305, which has two end sections 308, 334 and a third end section that not observable in the cross-sectional view of FIG. 6, which can be moved out of the housing 302. In a first position (shown in FIG. 6) of the sensor body 305, the end sections 308, 334 of the sensor body 305 are located within the housing 302 and in a second position (analogously shown FIG. 4 for the sensor arrangement 100) extend out of the housing 302.

The principal difference between the sensor arrangement 300 of the fourth example of an embodiment and the sensor arrangement 100 of the second example of an embodiment illustrated in FIGS. 3 and 4 lies in the embodiment of the pH-sensitive membrane 316 of the measuring half cell. The pH-sensitive membrane 316 is embedded in the end section 308 as an encircling ring of pH membrane glass in a housing part 309 forming the measuring half cell. Housing part 309 is composed of glass in the present example of an embodiment. Membrane 316 is fused or adhered in the housing part 309.

Sensor arrangement 300 is otherwise substantially identically embodied and can be operated in the same manner as the sensor arrangement 100 shown in FIGS. 3 and 4.

The invention claimed is:

1. A sensor arrangement comprising:
a housing connectable with a process container and including a guiding passageway and a chamber formed therein; and
a sensor body displaceable in the guiding passageway in an axial direction between a first position and a second position, the sensor body having at least one end section that can be translated out of the housing, the at least one end section including at least one sensor element configured to register a measured variable of a measured medium,
wherein, in the first position of the sensor body, the at least one sensor element is arranged within the chamber and, in the second position of the sensor body, outside of the housing, and
wherein the at least one end section of the sensor body includes a base and a peripheral surface, and the at least one sensor element is integrated into a housing wall of the sensor body that forms a part of the peripheral surface.

2. The sensor arrangement of claim 1, wherein the at least one sensor element is either one-piece with the housing wall or connected by material bonding with an opening of the housing wall such that the at least one sensor element closes the opening of the housing wall.

3. The sensor arrangement of claim 2, wherein the at least one sensor element comprises a membrane, which closes the chamber surrounded by the housing wall.

4. The sensor arrangement of claim 3, wherein the at least one sensor element is structured as an annular insert in the housing wall, extending around a rotational symmetry axis of the housing wall.

5. The sensor arrangement of claim 4, wherein a housing part has a cylindrical or annular shape and the at least one sensor element closes the housing part on an end as an appendage of the housing part, wherein the appendage is a capsule-shaped appendage or an appendage embodied as an annular cup.

6. The sensor arrangement of claim 1, wherein the sensor arrangement is a potentiometric sensor arrangement having a measuring half cell and a reference half cell.

7. The sensor arrangement of claim 6, wherein a measuring half cell chamber and a reference half cell chamber are formed in the sensor body.

8. The sensor arrangement of claim 7, wherein a portion of a wall of the measuring half cell chamber forms at least one part of the peripheral surface of the end section of the sensor body, and wherein the at least one sensor element includes an ion-selective membrane integrated into the portion of the wall of the measuring half cell chamber forming the part of the peripheral surface of the end section.

9. The sensor arrangement of claim 8, wherein the ion-selective membrane is a pH glass membrane.

10. The sensor arrangement of claim 7, wherein a portion of a wall of the reference half cell chamber forms at least one part of the peripheral surface of the end section of the sensor body, the portion of the wall of the reference half cell chamber having an electrochemical diaphragm arranged therein.

11. The sensor arrangement of claim 7, wherein the at least one end section of the sensor body is cylindrical, and wherein the measuring half cell chamber or the reference half cell chamber is formed in a first annular housing part of the sensor body, which surrounds at least one section of a second housing part of the sensor body.

12. The sensor arrangement of claim 7, wherein the sensor body has a plurality of cylindrical end sections structured to translate from the housing and extend substantially parallel to one another, wherein each of the end sections includes one section of a housing part of the sensor body, and wherein the measuring half cell chamber is formed in a housing part forming a first end section, and the reference half cell chamber is formed in a separate housing part forming a second end section.

13. The sensor arrangement of claim 12, wherein a further housing part of the sensor body forming a third end section includes a temperature sensor element.

14. The sensor arrangement of claim 1, wherein the at least one end section of the sensor body includes a temperature sensor element.

15. The sensor arrangement of claim 1, wherein the chamber formed in the housing is formed between the guiding passageway and the peripheral surface of the at least one end section of the sensor body, and wherein the chamber is bounded by a sealing element extending peripherally around the end section of the sensor body.

16. The sensor arrangement of claim 15, wherein the sealing element is disposed in the housing and bears against the peripheral surface of the at least one end section of the sensor body, and wherein the at least one sensor element travels over the sealing element as the sensor body translates from the first position into the second position.

17. The sensor arrangement of claim 16, wherein the at least one sealing element includes a peripheral protrusion structured to wipe off substances clinging to the peripheral surface or the at least one sensor element.

18. The sensor arrangement of claim 1, the sensor arrangement further comprising:
   a closable liquid inlet in fluid communication with the chamber through the housing; and
   a closable liquid outlet in fluid communication with the chamber through the housing.

19. The sensor arrangement of claim 18, wherein the chamber contains a calibration liquid or an electrolyte solution that contacts the at least one sensor element when the sensor body is in the first position.

* * * * *